(12) United States Patent
Zhang

(10) Patent No.: US 12,065,397 B2
(45) Date of Patent: Aug. 20, 2024

(54) BENZOATE DERIVATIVES

(71) Applicant: ZHEJIANG YUEJIA PHARMACEUTICALS CO., LTD, Wukang Town, Zhejiang Prov. (CN)

(72) Inventor: Jing Zhang, Shanghai (CN)

(73) Assignee: ZHEJIANG YUEJIA PHARMACEUTICALS CO., LTD, Zhejiang Prov. (CN)

( * ) Notice: Subject to any disclaimer, the term of this patent is extended or adjusted under 35 U.S.C. 154(b) by 0 days.

(21) Appl. No.: 18/154,520

(22) Filed: Jan. 13, 2023

(65) Prior Publication Data

US 2024/0124390 A1 Apr. 18, 2024

(30) Foreign Application Priority Data

Sep. 28, 2022 (CN) .......................... 202211195956.2

(51) Int. Cl.
| | |
|---|---|
| C07C 229/38 | (2006.01) |
| A61P 29/00 | (2006.01) |
| C07C 291/04 | (2006.01) |
| C07D 319/08 | (2006.01) |

(52) U.S. Cl.
CPC ............ *C07C 229/38* (2013.01); *A61P 29/00* (2018.01); *C07C 291/04* (2013.01); *C07D 319/08* (2013.01)

(58) Field of Classification Search
None
See application file for complete search history.

(56) References Cited

U.S. PATENT DOCUMENTS

| 3,365,483 A | 1/1968 | Jerzmanowska et al. |
| 2020/0360335 A1 | 11/2020 | Zhang |
| 2021/0387950 A1 | 12/2021 | Zhang |

FOREIGN PATENT DOCUMENTS

| CN | 101500983 A | | 8/2009 |
| CN | 104276962 A | | 1/2015 |
| CN | 106146326 A | | 11/2016 |
| CN | 109620800 A | | 4/2019 |
| CN | 115448905 | * | 12/2022 |
| EP | 3279182 A1 | | 2/2018 |
| JP | 2017119704 A | | 7/2017 |
| JP | 2018508581 A | | 3/2018 |
| WO | 2014139161 A1 | | 9/2014 |
| WO | 2019080693 A1 | | 5/2019 |
| WO | 2019095879 A1 | | 5/2019 |
| WO | 2021185382 A1 | | 9/2021 |

OTHER PUBLICATIONS

Bartzatt, R. et al., "Bifunctional constructs of aspirin and ibuprofen (non-steroidal anti-inflammatory drugs; NSAIDs) that express antibacterial and alkylation activities," Biotechnol. Appl. Biochem. (2001) 37, pp. 273-282. (Cited in EESR).
Extended European Search Report issued for European Patent Application No. 23151170.0, dated Aug. 22, 2023, 7 pages.
English translation of Search Report issued for Chinese Patent Application No. 202211195956.2, Mar. 5, 2023, 2 pages.
Notice of Reasons for Refusal issued for Japanese Patent Application No. 2023-003994, Dispatch Date: Oct. 30, 2023, 7 pages including English translation.

* cited by examiner

*Primary Examiner* — Po-Chih Chen
(74) *Attorney, Agent, or Firm* — HSML P.C.

(57) ABSTRACT

Disclosed are benzoate derivatives. Provided is a compound having a formula selected from the group consisting of following structures. The compound can be used for quality control over a 2-(diethylamino)ethyl 2-acetoxybenzoate hydrochloride product, and also for inflammation diminishment

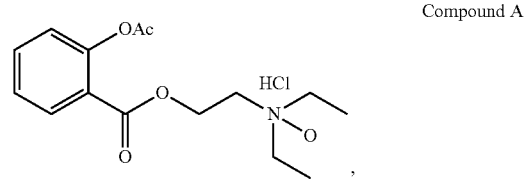
Compound A

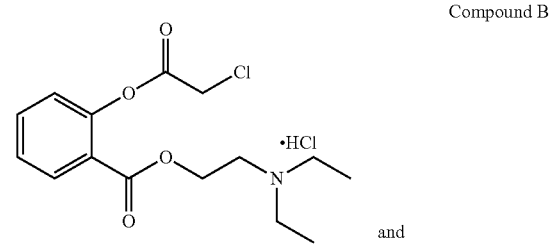
Compound B

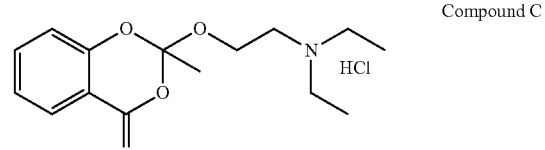
Compound C 6 Claims, 8 Drawing Sheets

BENZOATE DERIVATIVES

FIELD OF THE INVENTION

The present application relates to derivatives of 2-(diethylamino)ethyl 2-acetoxybenzoate hydrochloride.

BACKGROUND OF THE INVENTION

Compound 1, with a chemical name of 2-(diethylamino)ethyl 2-acetoxybenzoate hydrochloride, is clinically indicated for the treatment of diabetic peripheral neuropathic pain. Its derivatives with similar structures tend to become impurities that may be produced during its production. The impurities of the compound 1 have not been reported in the art.

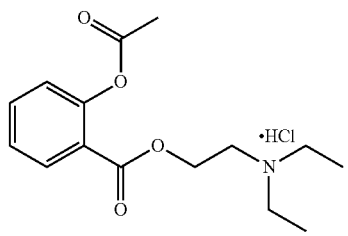

Compound 1

SUMMARY OF THE INVENTION

An object of the present application is to provide derivatives of 2-(diethylamino)ethyl 2-acetoxybenzoate hydrochloride, which can be used as impurities for quality control over 2-(diethylamino)ethyl 2-acetoxybenzoate hydrochloride products, and also have corresponding pharmaceutical uses, such as inflammation diminishment.

In one aspect, the present application provides a compound having a for selected from the group consisting of:

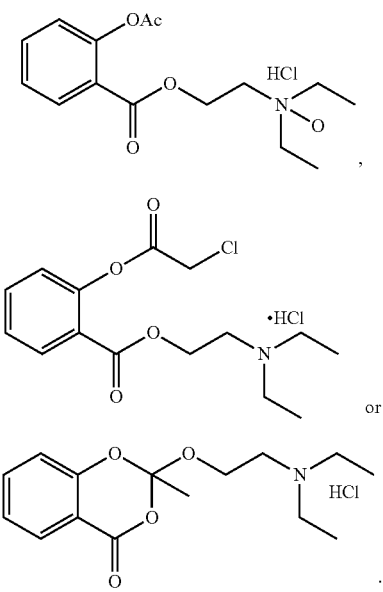

Compound A

Compound B or

Compound C

Ac in the structures above is acetyl.

In another aspect, the present application provides use of a compound in quality control over a product containing 2-(diethylamino)ethyl 2-acetoxybenzoate hydrochloride, said compound having a formula selected from the group consisting of:

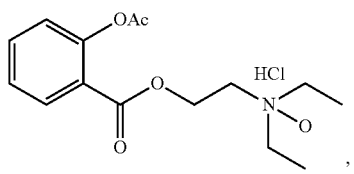

Compound A

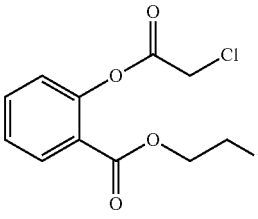

Compound B and/or

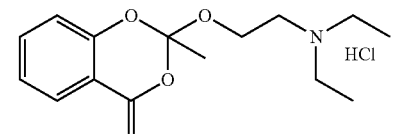

Compound C

In still another aspect, the present application provides a method for detecting an impurity in a 2-(diethylamino)ethyl 2-acetoxybenzoate hydrochloride product, said impurity being a compound having a formula selected from the group consisting of:

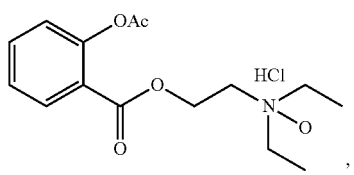

Compound A

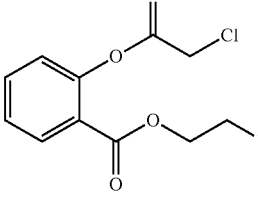

Compound B and/or

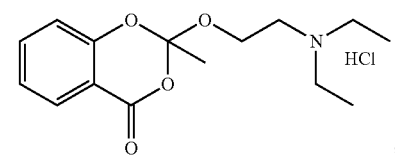

Compound C and said method comprising the steps of:
(1) providing said 2-(diethylamino)ethyl 2-acetoxybenzoate hydrochloride product;
(2) obtaining physical/chemical characteristic parameters of said compound A, compound B and/or compound C;

(3) performing a test on said 2-(diethylamino)ethyl 2-acetoxybenzoate hydrochloride product; and
(4) comparing physical/chemical characteristic parameters resulting from said test with said physical/chemical characteristic parameters of said compound A, compound B and/or compound C, and determining an impurity in said 2-(diethylamino)ethyl 2-acetoxybenzoate hydrochloride product.

In an example of the present application, said test in step (3) is preferably selected from the group consisting of a chromatography test, a nuclear magnetic resonance test, an infrared test, a mass spectrometry test, and/or an ultraviolet test.

In an example of the present application, said determining in step (4) comprises qualitative determining and/or quantitative determining.

In another aspect, the present application provides a method for detecting an impurity in a 2-(diethylamino)ethyl 2-acetoxybenzoate hydrochloride product, said impurity being a compound having a formula selected from the group consisting of:

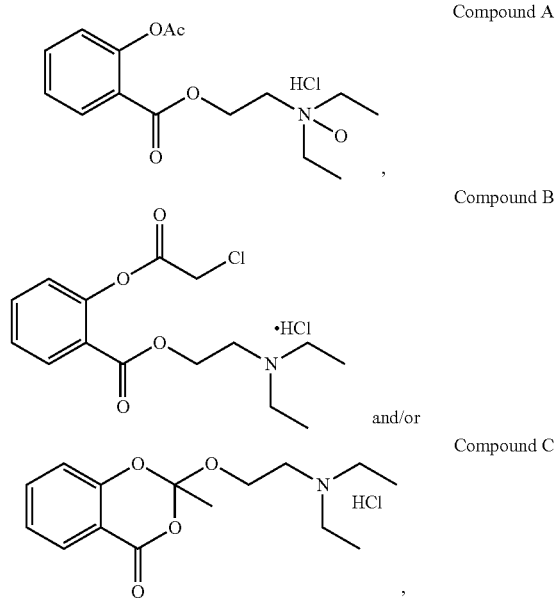

and said method comprising the steps of:
(1) providing said 2-(diethylamino)ethyl 2-acetoxybenzoate hydrochloride product;
(2) providing said compound A, compound B and/or compound C; and
(3) determining an impurity in said 2-(diethylamino)ethyl 2-acetoxybenzoate hydrochloride product by comparing test results of said 2-(diethylamino)ethyl 2-acetoxybenzoate hydrochloride product in step (1) with test results of said compound A, compound B and/or compound C in step (2).

In an example of the present application, said test in step (3) is preferably selected from the group consisting of a chromatography test, a nuclear magnetic resonance test, an infrared test, a mass spectrometry test, and/or an ultraviolet test.

In an example of the present application, said determining in step (3) comprises qualitative determining and/or quantitative determining.

The present application further provides a product containing 2-(diethylamino)ethyl 2-acetoxybenzoate hydrochloride, wherein said product comprises said 2-(diethylamino)ethyl 2-acetoxybenzoate hydrochloride having a content of not less than 98.00% by weight, and impurity compounds; said impurity compounds are selected from the group consisting of said compound A, compound B or compound C according to claim 1, or a combination thereof; and any one of said impurity compounds has a content of less than or equal to 0.50% by weight.

In an example of the present application, said product comprises said 2-(diethylamino)ethyl 2-acetoxybenzoate hydrochloride having a content of not less than 99.00% by weight.

In an example of the present application, any one of said impurity compounds has a content of less than or equal to 0.30% by weight; preferably, any one of said impurity compounds has a content of less than or equal to 0.20% by weight; and more preferably, any one of said impurity compounds has a content of less than or equal to 0.10% by weight.

The present application further provides use of a compound in preparation of an anti-inflammatory drug, said compound having a formula selected from the group consisting of:

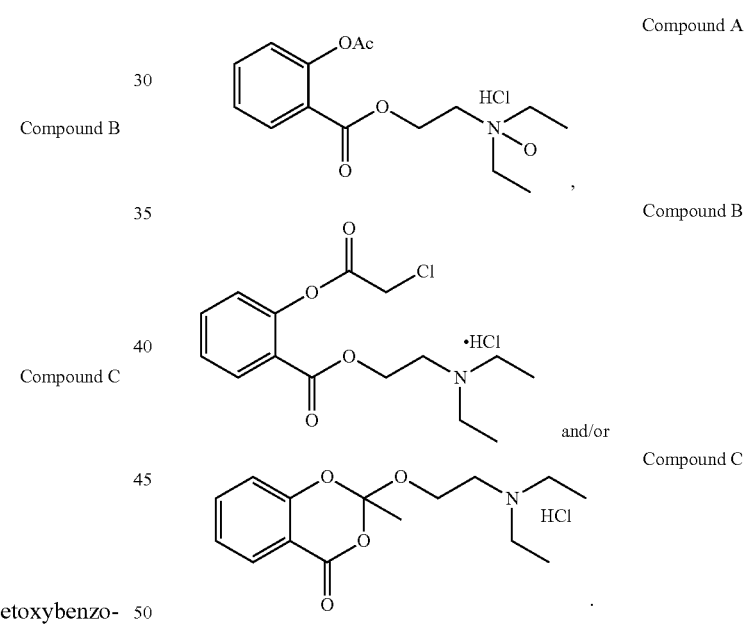

The compounds A, B and C are all critical components in the production and quality control of the compound 1, In addition, they have an anti-inflammatory effect pharmaceutically and have a high water solubility.

DETAILED DESCRIPTION OF THE PREFERRED EMBODIMENTS

Figure 1:
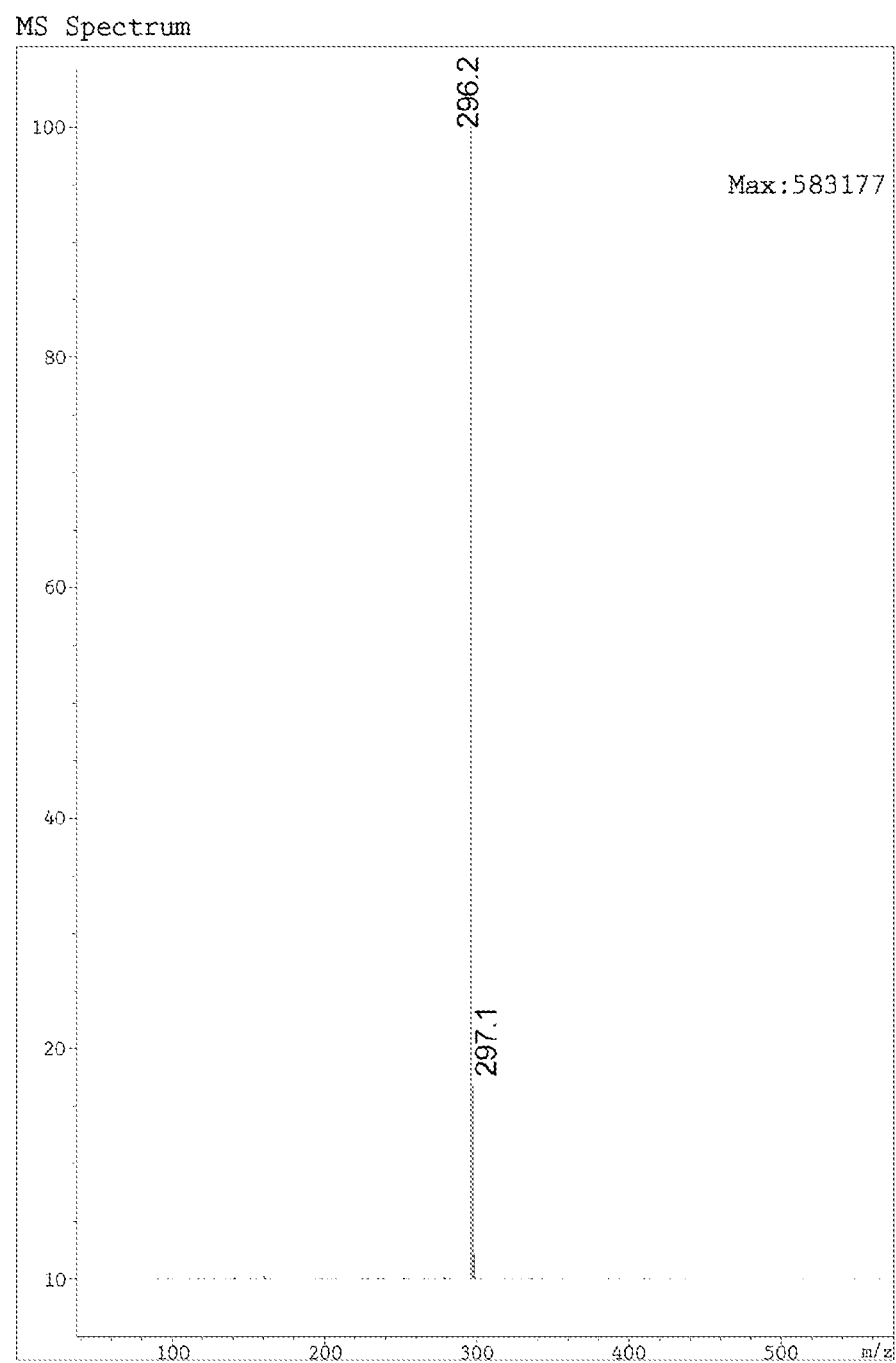
FIG. 1 shows a low-resolution electrospray ionization (ESI) mass spectrum of a compound A.

In the present description, the involved components or the preferred components thereof can be combined with each other to form a new technical solution, unless otherwise specified.

In the present description, all the embodiments and preferred embodiments mentioned can be combined with each other to form a new technical solution, unless otherwise specified.

In the present description, all the technical features and preferred features mentioned can be combined with each other to form a new technical solution, unless otherwise specified.

In the present description, the term "a/an" refers to "at least one", unless otherwise specified.

In the present description, all percentages, parts, etc. indicate weight, unless otherwise specified.

The "range" disclosed herein is defined by a lower limit or an upper limit or both. There may be one or more lower limits or one or more upper limits, respectively. A given range is defined by selecting a lower limit and an upper limit. The selected lower and upper limits define the boundaries of a specific range. All ranges that can be defined in this way are inclusive and combinable. That is, any lower limit can be combined with any upper limit to form a range.

Herein, the term "include" refers to the fact that a product may also contain any other components, which may be present at any content, as long as these components present at such contents are acceptable to a human body and have no negative effect on the activity of any active ingredient in the product of the present invention.

Herein, the term "inflammation diminishment" or "anti-inflammation" have the same meaning, both referring to inhibiting the production or release of inflammatory factors. By inhibiting the production or release of inflammatory factors, inflammation can be reduced to disappearance, and the pain caused by inflammation may be relieved at the same time.

In one aspect, the present application provides a compound having a formula selected from the group consisting of:

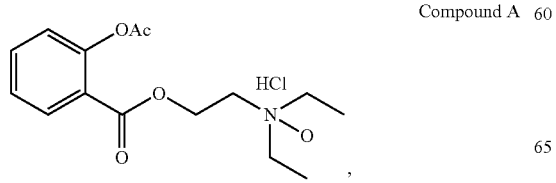

Compound A

-continued

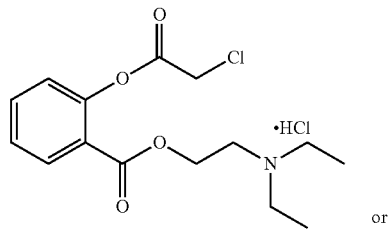

Compound B

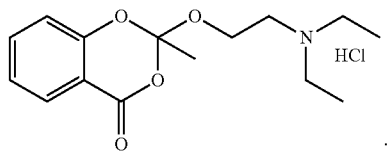

Compound C

Ac in the structures above is acetyl.

In another aspect, the present application provides use of a compound in quality control over a product containing 2-(diethylamino)ethyl 2-acetoxybenzoate hydrochloride, said compound having a formula selected from the group consisting of:

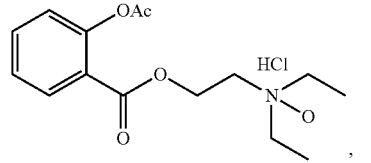

Compound A

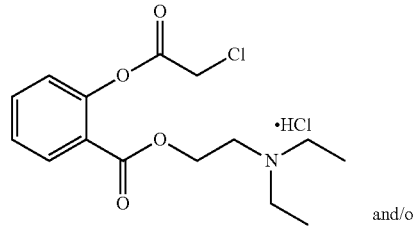

Compound B and/or

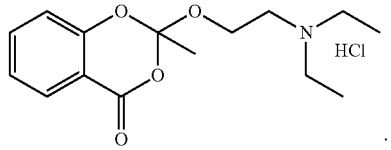

Compound C

In still another aspect, the present application provides a method for detecting an impurity in a 2-(diethylamino)ethyl 2-acetoxybenzoate hydrochloride product, said impurity being a compound having a formula selected from the group consisting of:

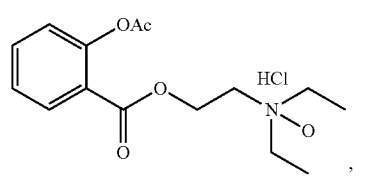

Compound A

-continued

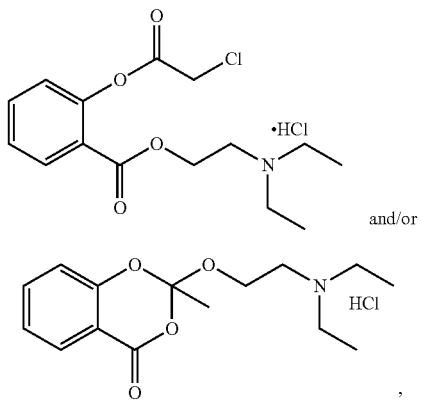

Compound B and/or

Compound C and said method comprising the steps of:
(1) providing said 2-(diethylamino)ethyl 2-acetoxybenzoate hydrochloride product;
(2) obtaining physical/chemical characteristic parameters of said compound A, compound B and/or compound C;
(3) performing a test on said 2-(diethylamino)ethyl 2-acetoxybenzoate hydrochloride product; and
(4) comparing physical/chemical characteristic parameters resulting from said test with said physical/chemical characteristic parameters of said compound A, compound B and/or compound C, and determining an impurity in said 2-(diethylamino)ethyl 2-acetoxybenzoate hydrochloride product.

In the present application, the step of providing 2-(diethylamino)ethyl 2-acetoxybenzoate hydrochloride product may be synthesizing in situ 2-(diethylamino)ethyl 2-acetoxybenzoate hydrochloride, or providing commercially available 2-(diethylamino)ethyl 2-acetoxybenzoate hydrochloride. The method for synthesizing 2-(diethylamino)ethyi 2-acetoxybenzoate hydrochloride is routine in the art. See, for example, Wo2019/095879A1, etc.

In the present application, the step of obtaining the physical/chemical characteristic parameters of the compound A, compound B and/or compound C includes, for example, but are not limited to, obtaining in situ the physical/chemical characteristic parameters of the compound A, compound B and/or compound C, or reading pre-stored physical/chemical characteristic parameters of the compound A, compound B and/or compound C, or obtaining the physical/chemical characteristic parameters of the compound A, compound B and/or compound according to the prior art (for example, but not limited to, technical manuals, prior literature, publicly available patent documents, or online data).

In an example, the in situ acquisition of the physical/chemical characteristic parameters of the compound A, compound B and/or compound C includes providing the compound A, compound B and/or compound C, and then measuring the physical/chemical characteristic parameters of the compound A, compound B and/or compound C.

In another example, the pre-stored physical/chemical characteristic parameters of the compound A, compound B and/or compound C include, but are not limited to, the physical/chemical characteristic parameters, stored in the form of data in a storage medium (for example, an external or internal memory), of the compound A, compound B and/or compound C.

In the present application, the physical/chemical characteristic parameters include, but are not limited to, chromatography, nuclear magnetic resonance (NMR), infrared, ultraviolet and/or mass spectrometry characteristic parameters, as well as relationships between these characteristic parameters and concentration (content, purity).

In an example of the present application, said test in step (3) is selected from the group consisting of a chromatography test, a nuclear magnetic resonance test, an infrared test, a mass spectrometry test, and/or an ultraviolet test. The method for performing a test (for example, chromatography, NMR, infrared, mass spectrometry and/or ultraviolet) on the 2-(diethylamino)ethyl 2-acetoxybenzoate hydrochloride product is routine, and the test may be performed easily by those of person skilled in the art according to the prior art.

In an example of the present application, said determining in step (4) comprises qualitative determining and/or quantitative determining. For example, the physical/chemical characteristic parameters of the 2-(diethylamino)ethyl 2-acetoxybenzoate hydrochloride product obtained in step (3) and the physical/chemical characteristic parameters (for example, the chromatography, NMR, infrared, mass spectrometry and/or ultraviolet characteristic parameters) of the compound A, compound B and/or compound C obtained in step (2) may be compared, to qualitatively or quantitatively determine an impurity (the compounds A, B and/or C) in the 2-(diethylamino)ethyl 2-acetoxybenzoate hydrochloride product.

In an example of the present application, said qualitative determining includes comparing the chromatography (for example, high-performance liquid chromatography), NMR, infrared, ultraviolet and/or mass spectrometry characteristic parameters. Examples include comparing the chromatography retention time, the NMR signals, the characteristic peaks in terms of infrared, the maximum absorption wavelength in terms of ultraviolet, and the characteristic peaks (or charge-to-mass ratio) in terms of mass spectrometry.

In an example of the present application, the quantitative determining includes: an internal standard method or a standard curve method.

In an example of the present application, the quantitative determining includes: (a) formulating standard substances of the compound A, compound B and/or compound C at different concentrations; (b) performing a test on the standard substances of the compound A, compound B and/or compound C at different concentrations for physical/chemical parameters; (c) drawing standard curves according to the physical/chemical parameters Obtained in step (b) and the concentrations Obtained in step (a); and (d) determining the concentration(s) of the compound A, compound B and/or compound C in the 2-(diethylamino)ethyl 2-acetoxybenzoate hydrochloride product according to the physical/chemical parameters of the 2-(diethylamino)ethyl 2-acetoxybenzoate hydrochloride product obtained in aforementioned step (3), and the aforementioned standard curves.

In another example of the present application, the quantitative determining includes:
(a) formulating reference substances of the compound A, compound B and/or compound C at certain concentrations;
(b) performing a test on the reference substances of the compound A, compound B and/or compound C for chromatograms, to determine the peak areas corresponding to the compound A, compound B and/or compound C; and (c) performing a test on a 2-(diethylamino)ethyl 2-acetoxybenzoate hydrochloride product for a chromatogram, and calculating the concentration(s) of the compound A, compound B and/or compound C according to the following formula:

concentration of the compound $A, B, C$ (%) =

$$\frac{\frac{A_{sample}}{A_{STD}} \times \frac{M_{STD} \times W}{V_{STD}} \times V_{sample}}{M_{sample}} \times 100\%$$

In the formula:
$A_{sample}$ represents the peak area of the compound A or B or C in a test sample solution;
$A_{STD}$ represents the peak area of the compound A or B or C in a reference substance solution of the compound A or B or C;
$M_{sample}$ represents the weight (mg) of a test sample;
$M_{STD}$ represents the weight (mg) of the reference substance of the compound A or B or C;
$V_{sample}$ represents the volume (mL) of the test sample solution;
$V_{STD}$ represents the volume (mL) of the reference substance solution of the compound A or B or C; and
W represents the content (calculated as 100.0% in case of above 100%) of the reference substance of the compound A or B or C.

In another aspect, the present application provides a method for detecting an impurity in a 2-(diethylamino)ethyl 2-acetoxybenzoate hydrochloride product, said impurity being a compound having a formula selected from the group consisting of:

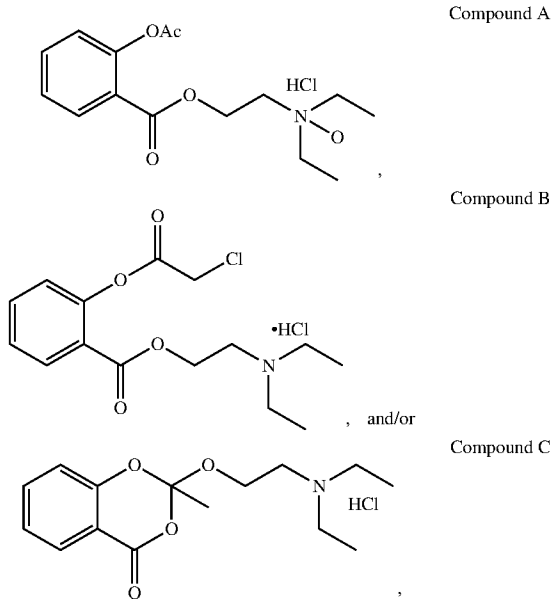

Compound A

Compound B

, and/or

Compound C and said method comprising the steps of:
(1) providing said 2-(diethylamino)ethyl 2-acetoxybenzoate hydrochloride product;
(2) providing said compound A, compound B and/or compound C; and
(3) determining an impurity in said 2-(diethylamino)ethyl 2-acetoxybenzoate hydrochloride product by comparing test results of said 2-(diethylamino)ethyl 2-acetoxybenzoate hydrochloride product in step (1) with test results of said compound A, compound B and/or compound C in step (2).

In the present application, the step of providing 2-(diethylamino)ethyl 2-acetoxybenzoate hydrochloride product may be synthesizing in situ 2-(diethylamino)ethyl 2-acetoxybenzoate hydrochloride, or providing commercially available 2-(diethylamino)ethyl 2-acetoxybenzoate hydrochloride. The method for synthesizing 2-(diethylamino)ethyl 2-acetoxybenzoate hydrochloride is routine in the art. See, for example, WO2019/095879A1, etc.

In the present application, the provision of the compound A, compound B and/or compound C includes synthesizing in situ the compound A, compound B and/or compound C, or obtaining the compound A, compound B and/or compound C (commercially available or stored as a standard substance) that are/is already synthesized.

In an example of the present application, said test in step (3) is preferably selected from the group consisting of a chromatography test, a nuclear magnetic resonance test, an infrared test, a mass spectrometry test, and/or an ultraviolet test. The method for performing a test (for example, chromatography, NMR, infrared, mass spectrometry and/or ultraviolet) on the 2-(diethylamino)ethyl 2-acetoxybenzoate hydrochloride product as well as on the compound A, compound B and/or compound C is routine, and the test may be performed easily by those of person skilled in the art according to the prior art.

In an example of the present application, said determining in step (3) comprises qualitative determining and/or quantitative determining. For example, the obtained physical/chemical characteristic parameters of the 2-(diethylamino)ethyl 2-acetoxybenzoate hydrochloride product and the obtained physical/chemical characteristic parameters (for example, the chromatography, NMR, infrared, mass spectrometry and/or ultraviolet characteristic parameters) of the compound A, compound B and/or compound C may be compared, to qualitatively or quantitatively determine an impurity (the compounds A, B and/or C) in the 2-(diethylamino)ethyl 2-acetoxybenzoate hydrochloride product.

In an example of the present application, said qualitative determining includes comparing the chromatography (for example, high-performance liquid chromatography), NMR, infrared, ultraviolet and/or mass spectrometry characteristic parameters.

Examples include comparing the chromatography retention time, the NMR signals, the characteristic peaks in terms of infrared, the maximum absorption wavelength in terms of ultraviolet, and the characteristic peaks (or charge-to-mass ratio) in terms of mass spectrometry.

In an example of the present application, the quantitative determining includes: an internal standard method or a standard curve method.

In an example of the present application, the quantitative determining includes: (a) formulating standard substances of the compound A, compound B and/or compound C at different concentrations; (b) performing a test on the standard substances of the compound A, compound B and/or compound C at different concentrations for physical/chemical parameters; (c) drawing standard curves according to the physical/chemical parameters obtained in step (b) and the concentrations obtained in step (a); and (d) determining the concentration(s) of the compound A, compound B and/or compound C in the 2-(diethylamino)ethyl 2-acetoxybenzoate hydrochloride product according to the physical/chemical parameters of the 2-(diethylamino)ethyl 2-acetoxybenzoate hydrochloride product obtained in aforementioned step (3), and the aforementioned standard curves.

In another example of the present application, the quantitative determining includes:
(a) formulating reference substances of the compound A, compound B and/or compound C at certain concentrations;

(b) performing a test on the reference substances of the compound A, compound B and/or compound C for chromatograms, to determine the peak areas corresponding to the compound A, compound B and/or compound C; and (c) performing a test on a 2-(diethylamino)ethyl 2-acetoxybenzoate hydrochloride product for a chromatogram, and calculating the concentration(s) of the compound A, compound B and/or compound C according to the following formula:

$$\text{concentration of the compound } A, B, C\ (\%) = \frac{\dfrac{A_{sample}}{A_{STD}} \times \dfrac{M_{STD} \times W}{V_{STD}} \times V_{sample}}{M_{sample}} \times 100\%$$

In the formula:
$A_{sample}$ represents the peak area of the compound A or B or C in a test sample solution;
$A_{STD}$ represents the peak area of the compound A or B or C in a reference substance solution of the compound A or B or C;
$M_{sample}$ represents the weight (mg) of a test sample;
$M_{STD}$ represents the weight (mg) of the reference substance of the compound A or B or C;
$V_{sample}$ represents the volume (mL) of the test sample solution;
$V_{STD}$ represents the volume (mL) of the reference substance solution of the compound A or B or C; and
W represents the content (calculated as 100.0% in case of above 100%) of the reference substance of the compound A or B or C.

The present application further provides a product containing 2-(diethylamino)ethyl 2-acetoxybenzoate hydrochloride. The product comprises the 2-(diethylamino)ethyl 2-acetoxybenzoate hydrochloride having a content of not less than 98.00% by weight (for example, 98.00% to 99.5% by weight), and impurity compounds; the impurity compounds are selected from the group consisting of the compound A, compound B or compound C, or a combination thereof; and any one of the impurity compounds has a content of less than or equal to 0.50% by weight (for example, 0.01% to 0.50% by weight).

In an example of the present application, the product includes the 2-(diethylamino)ethyl 2-acetoxybenzoate hydrochloride having a content of not less than 99.00% by weight (for example, 99.00% to 99.5% by weight).

In an example of the present application, any one of the impurity compounds has a content of less than or equal to 0.30% by weight (for example, 0.01% to 0.30% by weight); preferably, any one of the impurity compounds has a content of less than or equal to 0.2% by weight (for example, 0.01% to 0.20% by weight); and more preferably, any one of the impurity compounds has a content of less than or equal to 0.10% by weight (for example, 0.01% to 0.10% by weight).

The present application further provides use of a compound in preparation of an anti-inflammatory drug, said compound having a formula selected from the group consisting of:

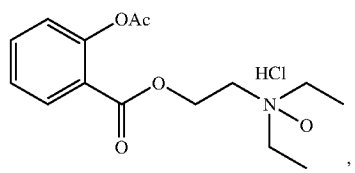

Compound A

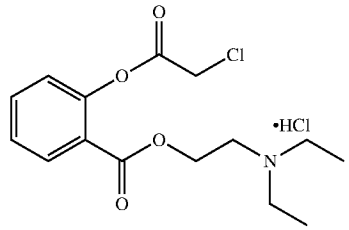

Compound B

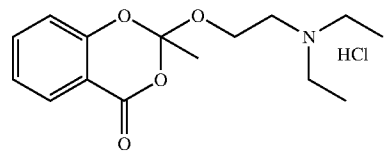

and/or

Compound C

In another aspect, the present application provides a method for inflammation diminishment. The method includes administering a compound to an individual in need of treatment, the compound having a formula selected from the group consisting of:

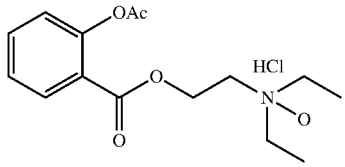

Compound A

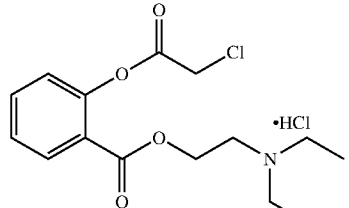

Compound B

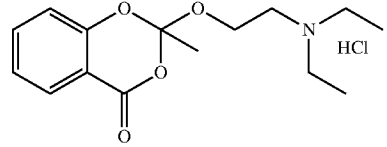

and/or

Compound C

The present invention will be further described in detail below in conjunction with the embodiments. However, it should be understood that these examples are enumerated merely for an illustrative purpose, and are not intended to limit the scope of the present invention.

Example 1

In this example, a compound A was synthesized and characterized with the following methods:

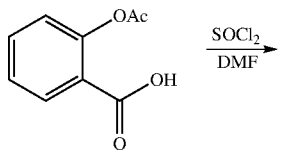

-continued

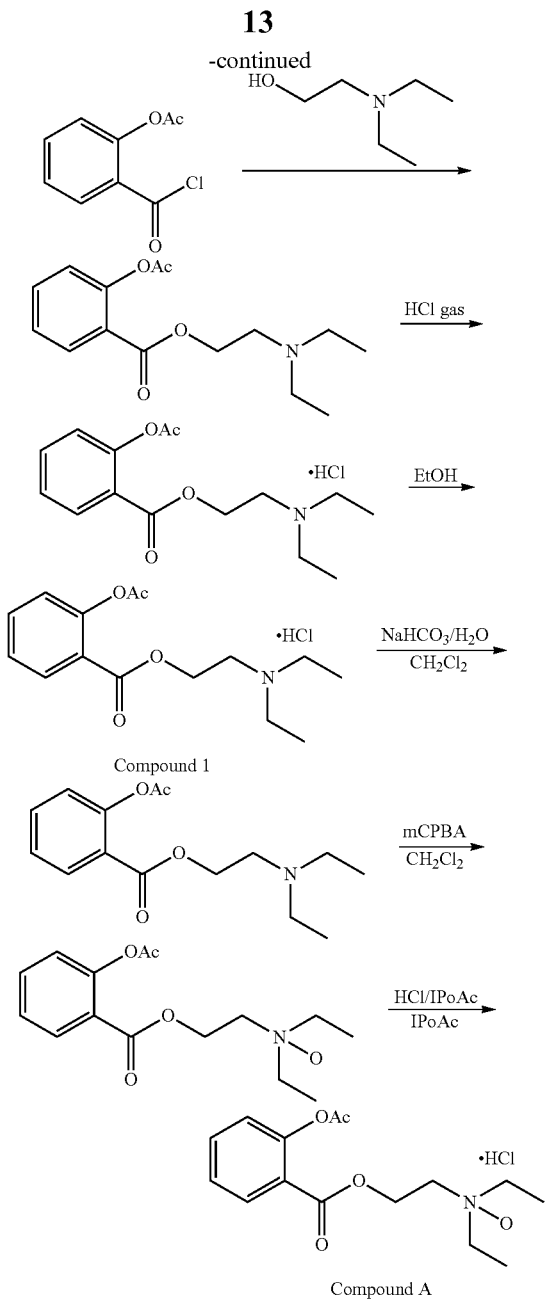

Compound 1

Compound A

1) Aspirin, as a raw material, reacted with thionyl chloride in the presence of dimethylformamide to obtain o-acetylsalicylinyl chloride; the o-acetylsalicylinyl chloride then reacted with diethylaminoethanol to generate 2-(diethylamino)-ethyl 2-acetoxybenzoate, which finally reacted with a hydrochloric gas to obtain the crude product of 2-(diethylamino) ethyl 2-acetoxybenzoate hydrochloride (namely, the compound 1); and the crude product was recrystallized with ethanol to obtain the raw material, 2-(diethylamino) ethyl 2-acetoxybenzoate hydrochloride.
2) 110 g of the compound 1 was weighed and placed in an Erlenmeyer flask, and 700 mL of purified water was added to dissolve the sample; and under magnetic stirring in an ice bath, 35 g of sodium bicarbonate was slowly added, with a small amount of air bubbles escaped. Stirring continued until no significant air bubbles were generated.
3) 500 mL of dichloromethane was added, and a large number of air bubbles escaped from a water layer; stirring continued until no significant air bubbles were generated, and the reaction was terminated; the resultant was extracted and dispensed, and 500 mL of dichloromethane was added to the water layer for extraction and dispensing again; and the organic phases were combined and dried with anhydrous sodium sulfate to obtain a free alkali drying solution.
4) 78 g of meta-chloroperoxybenzoic acid was weighed and prepared into a suspension using 500 mL of dichloromethane; and the suspension was slowly poured into the free alkali drying solution, at a pouring rate controlled to prevent bumping. Reaction proceeded for 1 h. After the reaction was completed, insolubles were removed by filtration, and most of the solvent was removed by rotary evaporation to obtain a yellow oily liquid.
5) 1500 mL of isopropyl acetate was added to the oily liquid above to form an emulsion to dissolve the crude product. Hydrogen chloride in isopropyl acetate solution (converted to about 1.1 eq of the amount of the compound 1 added) was slowly dropwise added into the reaction system, and the resultant was filtered to obtain a compound A (purity: 98.26%).
6) In this example, the compound A was characterized as follows: $^1$H NMR (500 MHz, CDCl$_3$) δ 7.94 (dd, 7.8, 1.4 Hz, 1H), 7.62 (td, J=8.0, 1.5 Hz, 1H), 7.35 (t, J=7.2 Hz, 1H), 7.20-7.06 (m, 1H), 4.90-4.72 (m, 2H), 4.24-4.06 (m, 2H), 3.84 (ddt, J=25.0, 13.4, 7.0 Hz, 4H), 2.35 (s, 3H), 1.40 (t, J=7.2 Hz, 6H).
7) in this example, the compound A was characterized as follows: $^{13}$C NMR (101 MHz, CDCl$_3$) δ (ppm)=169.51, 163.42, 150.58, 134.53, 130.88, 130.84, 126.05, 123.69, 121.86, 77.32, 77.00, 76.68, 61.45, 59.24, 57.41, 20.93, 20.88, 8.05.
8) in this example, the compound A may also be qualitatively analyzed by infrared chromatography. Compared with the compound 1, the infrared characteristics of the compound A are significantly different in the presence of stretching vibrations of N—O bonds, with a peak range occurring at 1500 cm$^{-1}$-1690 cm$^{-1}$. In addition, the compound A has the N—O bonds formed in structure, and its ammonium salt has the characteristic peak (2700-2500 cm$^{-1}$) that is obviously different from the compound 1 in peak shape and absorption intensity.
9) In this example, the compound A may also be qualitatively analyzed by ultraviolet chromatography. After being dissolved in methanol, the compound A shows the maximum absorption wavelength at 225 nm and the second maximum absorption wavelength at 279 nm in the ultraviolet spectrum.
10) in this example, the compound A may also be qualitatively measured by mass spectrometry. The mass spectrum of the compound A is shown in FIG. 1, in which the ionization mode is electrospray ionization (ESI), the ion mode is positive ion mode, and the m/z value of [M-Cl]$^+$ in the sample is measured as 296.2.
11) In this example, the compound A may also be quantitatively analyzed by an NMR internal standard method, where an internal standard substance should be selected to ensure no interference with the signal peak of the measured substance, and tetramethylsilane (TMS) may be used as the internal standard substance.

Example 2

In this example, a compound B was synthesized and characterized with a method including the following steps:

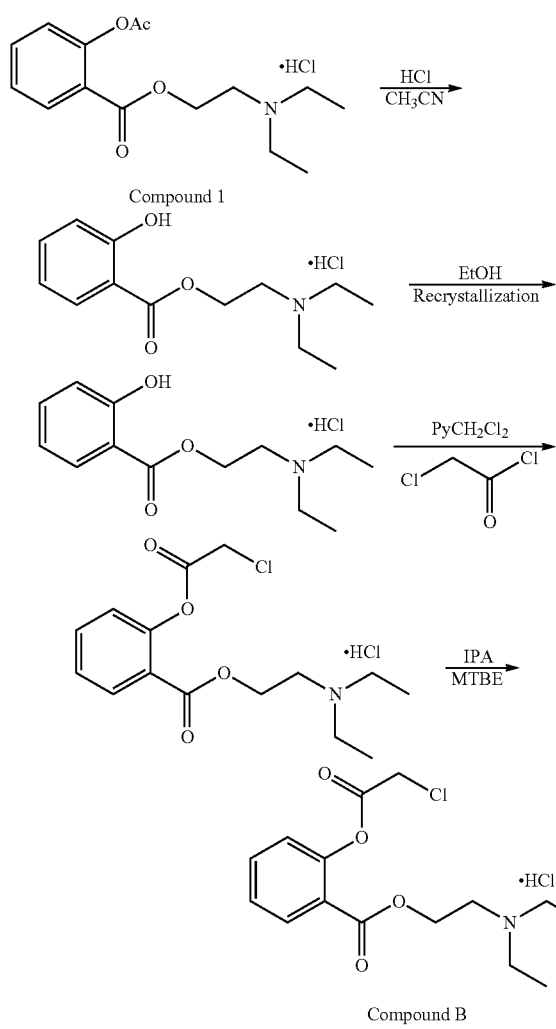

Figure 2:
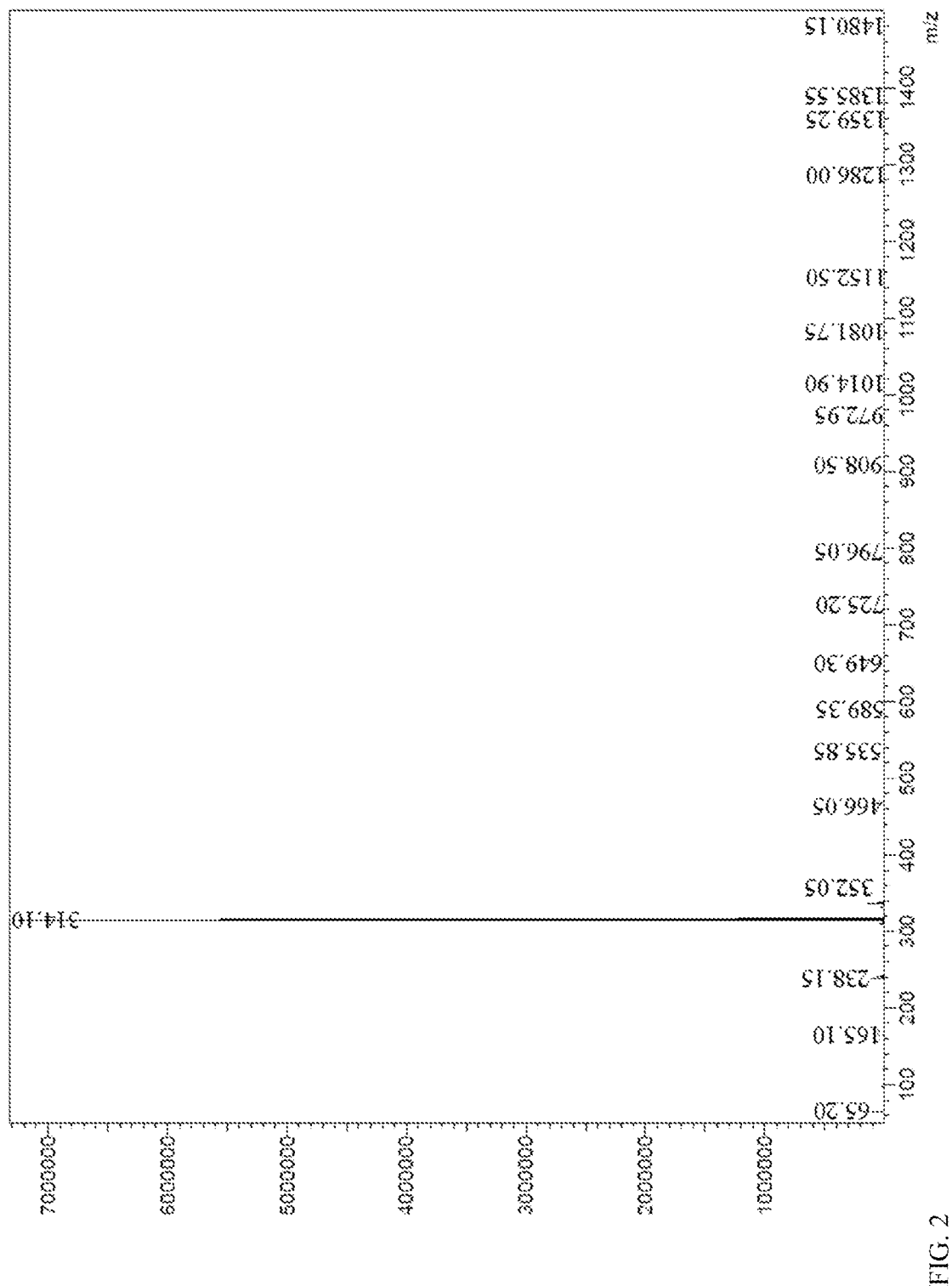
FIG. 2 shows a low-resolution ESI mass spectrum of a compound B.

1) 200 g of the compound 1 was weighed out, 500 mL acetonitrile and 50 mL of concentrated hydrochloric acid were added, and the mixture was stirred at room temperature for 72 h. The solvent was removed by distillation under reduced pressure at 30-40° C.; 600 ml of ethanol was added; the mixture was stirred and heated to 50-60° C., and kept at the current temperature for 1 h to dissolve all solids; the mixture stood to room temperature, and was kept at the current temperature for 12 h, filtered by suction, and washed with 100 mL ethanol to obtain a wet product; and the wet product was dried at 60° C. for 12 h, to obtain 2-acetoxyphenol-2-(diethylamino)ethyl ester hydrochloride.
2) 250 g of 2-acetoxyphenol-2-(diethylamino)ethyl ester hydrochloride was weighed and placed into a four-necked flask; 2100 mL of dichloromethane was added; and the mixture was stirred mechanically, and cooled down to 0-10° C. in an ice bath.
3) 96 g of pyridine was weighed in a constant-pressure dropping funnel to be slowly dropwise added to the reaction system; and after the dropwise addition, the stirring continued for 10 min.
4) With the internal temperature of 0-10° C., 137.5 g of chloroacetyl chloride was weighed in the constant-pressure dropping funnel to be slowly dropwise added to the reaction system, during which the internal temperature was controlled to 0-10° C., and after the dropwise addition, stirring continued for 2-4 h.
5) The reaction liquid was transferred to a single-necked flask, and concentrated under reduced pressure until no fraction was evaporated basically, and a light yellow viscous solid was obtained.
6) 400 mL of isopropanol and 800 mL of methyl Certbutyl ether were added to the single-necked flask, respectively, during which the internal temperature was controlled to 0-10° C.; and the mixture was beaten for 1-2 h.
7) The beating was stopped; the mixture was filtered by suction under reduced pressure; and the filter cake was washed several times by using 400 mL of methyl tert-butyl ether to obtain an off-white solid wet product.
8) The wet product was placed in a vacuum drying oven and dried under reduced pressure to obtain an off-white crude product.
9) The above crude product was weighed and placed into a three-necked flask; 400 mL of isopropanol was added; and the mixture was stirred mechanically, and heated up in an oil bath.
10) The dissolution was incomplete in the system at the internal temperature of 75° C.; with the current temperature maintained, stirring was performed for 15 min, and the temperature gradually dropped to 0-10° C., during which methyl tert-butyl ether could be replenished.
11) Suction filtration was performed under reduced pressure to obtain an off-white solid wet product.
12) The wet product was placed in a vacuum drying oven and dried under reduced pressure to obtain an off-white solid compound B (purity: 98.4%).
13) In this example, the compound B was characterized as follows: $^1$H NMR (400 MHz, DMSO-d$_6$) δ11.42 (s, 1H), 8.13 (dd, J=7.9, 1.7 Hz, 1H), 7.74 (td, J=7.8, 1.7 Hz, 1H), 7.46 (td, J=7.6, 1.2 Hz, 1H), 7.32 (d, J=8.2 Hz, 1H), 4.64 (t, J=5.3 Hz, 2H), 3.48 (d, J=5.2 Hz, 2H), 3.17 (s, 1H), 1.25 (t, J=7.2 Hz, 6H).
14) In this example, the compound B was characterized as follows: $^{13}$C NMR (101 MHz, DMSO-d$_6$) δ (ppm)=166.71, 163.59, 150.19, 135.30, 132.21, 127.30, 124.21, 122.44, 59.98, 49.44, 47.27, 41.78, 8.84.
15) In this example, the compound B may also be qualitatively analyzed by infrared chromatography. Compared with the compound 1, the infrared characteristics of the compound A are significantly different in the presence of stretching vibrations of C—Cl bonds, with a fingerprint region peak range occurring at 800-600 cm$^{-1}$.
16) in this example, the compound B may also be qualitatively analyzed by ultraviolet chromatography. After being dissolved in methanol, the compound B shows the maximum absorption wavelength at 222 nm and the second maximum absorption wavelength at 243 nm in the ultraviolet spectrum.
17) In this example, the compound B may also be qualitatively measured by mass spectrometry. The mass spectrum of the compound A is shown in FIG. 2. The ionization mode is ESI, the ion mode is positive ion mode, and the m/z value of [M-Cl]$^+$ in the sample is measured as 314.1.
18) In this example, the compound B may also be quantitatively analyzed by an NMR internal standard method, where an internal standard substance should be selected to ensure no interference with the signal peak of the measured substance, and TMS may be used as the internal standard substance.

Example 3

In this example, a compound C was synthesized and characterized with a method including the following steps:

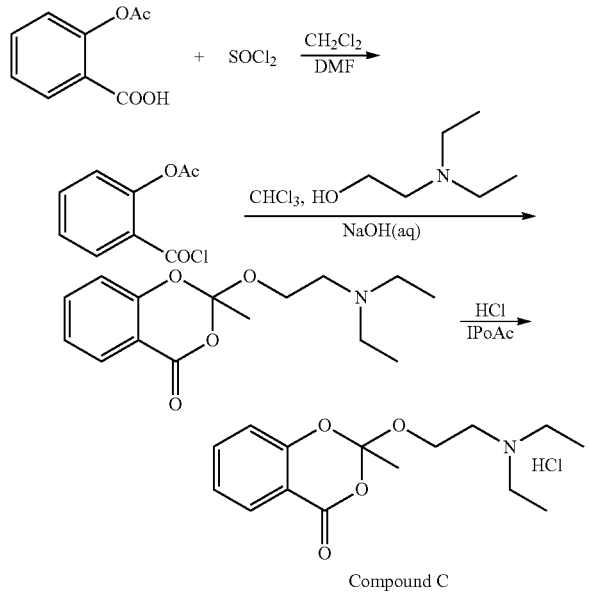

Compound C 1) 180 g of aspirin was weighed into a four-necked flask; dichloromethane and N,N-dimethylformamide (1 mL) were added; the mixture was stirred, and heated up to about 30-40° C. in the oil bath.
2) 144 g of thionyl chloride was weighed in a constant-pressure dropping funnel to be slowly dropwise added into the reaction system. After dropwise addition, stirring was continued for 1 h.
3) The reaction is terminated; the reaction liquid was transferred into a single-necked flask; and the solvent was removed by concentration under reduced pressure to obtain a concentrated solution of acyl chloride.
4) The acyl chloride was placed in a four-necked flask; 100 mL of chloroform was added and dissolved; the mixture was stirred mechanically, and heated up in the oil bath.
5) 118 g of diethylaminoethanol (1.0 eq.) was slowly dropwise added, during which the mixture was heated up for reflux.
6) After dropwise addition, reaction proceeded for 1 h.
7) The reaction was terminated, and the reaction mixture was cooled down to room temperature. Sodium hydroxide in ice-water solution, containing 40 g of sodium hydroxide, was added to the system for an alkaline (pH: about 8) system; the system was stirred and dispensed; and the organic phase was washed with 400 mL of saturated sodium chloride, and dried overnight with 40 g of anhydrous sodium sulfate. The extract liquid was filtered and concentrated to obtain a concentrated solution.
8) 80 g of the concentrated solution was placed in a four-necked flask; 200 mL of isopropyl acetate was added; and the mixture was stirred mechanically at room temperature.
9) HCl gas was slowly injected; a yellow oily matter first precipitated; and when pH<7.0, solids began to precipitate and gradually increased. The pH value was monitored and controlled to be more than 6.0. After gas injection, stirring continued for 30 minutes, and then filtration was performed.
10) The filter cake was transferred into an Erlenmeyer flask, 100 mL of acetonitrile was added, and the mixture was heated for dissolution. The resultant was cooled to room temperature, isopropyl acetate was added, and the mixture was mixed well under shaking, until turbidness appeared without any dissolution after shaking. The system was heated until the liquid was clear, and cooled down to room temperature under stirring, during which a large amount of granular solids precipitated. The solids were filtered, and the filter cake was washed with a small amount of isopropyl acetate and dried for 2 h to obtain the compound C (purity: 99.4%).
11) in this example, the compound C was characterized as follows: $^1$H NMR (500 MHz, CDCl$_3$) δ 11.5.(brs, 1H,), δ 7.96 (dd, 1H, J=7.66(dt, 1H, J=7.6 Hz), 7.22 (t, 4H, J=7.6 Hz), 7.11 (d, 4H, J=7.8 Hz), 4.30 (m, 2H), 3.26 (t, J=5.0 Hz), 3.07 (brs, 4H), 1.89 (s, 3H), 1.31 (t, 6H, J=6.0 Hz).
12) In this example, the compound C was characterized as follows: $^{13}$C NMR (125 MHz, CDCl$_3$) δ (ppm)=136.81, 129.17, 123.47, 116.99, 22.37, 58.76, 49.75, 46.89, 8.40.
13) in this example, the compound C may also be qualitatively analyzed by infrared chromatography, where 3489.5 cm$^{-1}$ represents the overtone signal of the C=O stretching vibration of benzoate, corresponding to the C=O stretching vibration of benzoate at 1755.0 cm$^{-1}$ indicating the possibility of a benzoate structure in the molecule. 3003.3 cm$^{-1}$, and 2948.3 cm$^{-1}$: represent the C—H stretching vibration of methyl or methylene, indicating the possible presence of a methyl or methylene structure in the molecule, 2578.9 cm$^{-1}$ and 2478.7 cm$^{-1}$: represent the N—H stretching vibration of ammonium salt, indicating the possible presence of an ammonium salt structure in the molecule. 1614.0 cm$^{-1}$, 1591.4 cm$^{-1}$, and 1466.5 cm$^{-1}$ represents the C=C stretching vibration of a benzene ring skeleton, indicating the possible presence of a benzene ring structure in the molecule. 1393.8 cm$^{-1}$ and 1302.4 cm$^{-1}$ represent the C—H bending vibration of methyl, indicating the possible presence of a methyl structure in the molecule. 1270.5 cm$^{-1}$ and 1254.5 cm$^{-1}$ represent the C—O bending vibration of benzoate, indicating the possible presence of a benzoate structure in the molecule.
14) in this example, the compound C may also be qualitatively analyzed by ultraviolet chromatography. After being dissolved in methanol, the compound C shows the maximum absorption wavelength at 205 nm and the second maximum absorption wavelength at 237 nm in the ultraviolet spectrum.
15) In this example, the compound C may also be qualitatively measured by high-resolution mass spectrometry. The ionization mode is ESI, the ion mode is positive ion mode, and the accurate mass value m/z of [M-Cl]$^+$ in the sample is measured as 280.1.
16) In this example, the compound C may also be quantitatively analyzed by an NMR internal standard method, where an internal standard substance should be selected to ensure no interference with the signal peak of the measured substance, and TMS may be used as the internal standard substance.

Example 4

This example illustrates, by way of example, the use of the compounds A, B and C as impurity reference substances in the quality control over the compound 1 and in the control of the production process of the intermediates of the compound 1.

1. Preparation Process of Compound 1:

For the method for preparing the compound 1 (2-(diethylamino)ethyl 2-acetoxybenzoate hydrochloride), a reference can be made to Example 1, or to the prior art.

2. Source and Detection Method of Compound A 2.1 The testing results of the finished product of the compound 1 after long-term storage and the results of a strong degradation experiment both show that tertiary amine in the structure of compound 1 will undergo oxidation reaction due to the presence of oxidants (such as oxygen in the air), to obtain the nitrogen oxide of compound 1, namely, the compound A. To study the stability of the compound 1 during long-term storage and transportation, there is a need to develop an analytical method for detecting the content of the compound A (impurity) so as to control the quality of the finished product of the compound 1.

2.2 Detection method of compound A 2.2.1 Chromatographic conditions: according to high-performance liquid chromatography, octadecylsilane bonded silica gel was used as a filler (250 mm×4.6 mm, 5 μm); the column temperature was 33° C.; the flow rate was 1.0 mL/min; the injection volume was 10 μL; the detection wavelength is 276 nm; and the mobile phase was buffered saline solution-methanol-glacial acetic acid (66:24:10).

2.2.2 Formulation of solutions:

1) Test sample solution: about 100 mg of the compound 1 stored for a long time was taken as a test sample, weighed accurately, and placed in a 110 mL volumetric flask; methanol was added for dissolution to a constant volume at a given scale; and the mixture was shaken well to be used as a test sample solution, which might be in duplicate upon choice.

2) Reference substance solution of compound A: about 20 mg of the reference substance of the compound A was taken, weighed accurately, and placed in a 100 mL volumetric flask; methanol was added for dissolution to a constant volume at a given scale; and the mixture was shaken well and used as a reference substance solution of the compound A.

2.2.3 Determination method: the reference substance solution of the compound A and the test sample solution were accurately weighed out, and respectively injected into a liquid chromatograph; and the chromatogram was recorded, where the chromatogram was recorded till 3 times the retention time of the principal component peak.

2.2.4 Calculation of content $$\text{content of the compound } A\ (\%) = \frac{\frac{A_{sample}}{A_{STD}} \times \frac{M_{STD} \times W}{V_{STD}} \times V_{sample}}{M_{sample}} \times 100\% \quad \text{(Formula I)}$$

In the formula;

$A_{sample}$ represents the peak area of the compound A in the test sample solution;

$A_{STD}$ represents the peak area of the compound A in the reference substance solution of the compound A;

$M_{sample}$ represents the weight (mg) of a test sample;

$M_{STD}$ represents the weight (mg) of the reference substance of the compound A;

$V_{sample}$ represents the volume (mL) of the test sample solution;

$V_{STD}$ represents the volume (mL) of the reference substance solution of the compound A; and W represents the content (calculated as 100.0% in case of above 100%) of the reference substance of the compound A.

Figure 3:
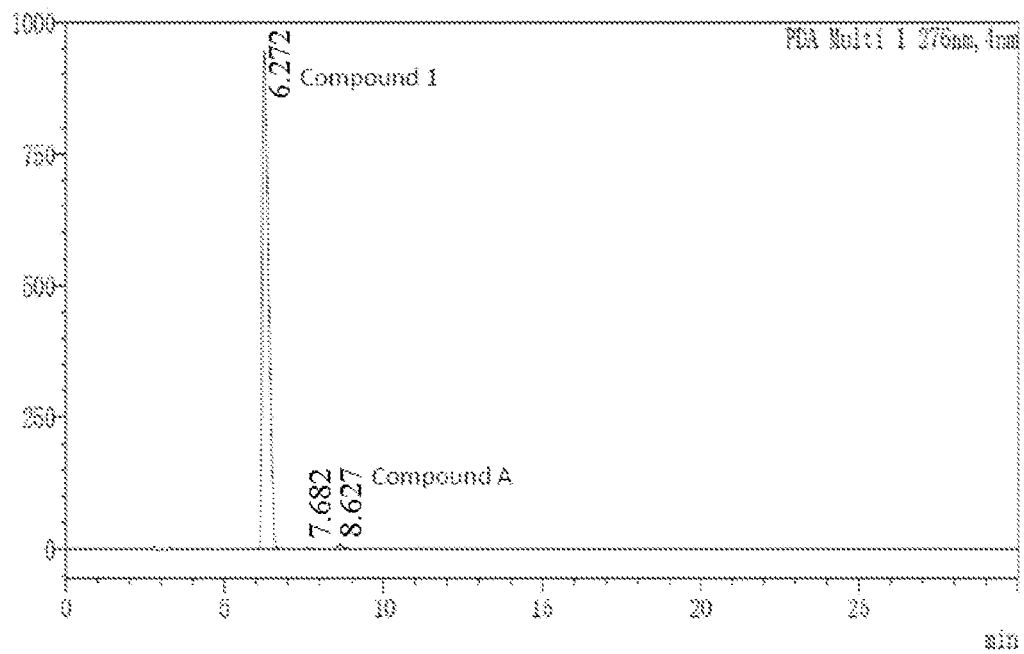
FIG. 3 shows a chromatogram of a compound 1 stored for a long time.
Figure 4:
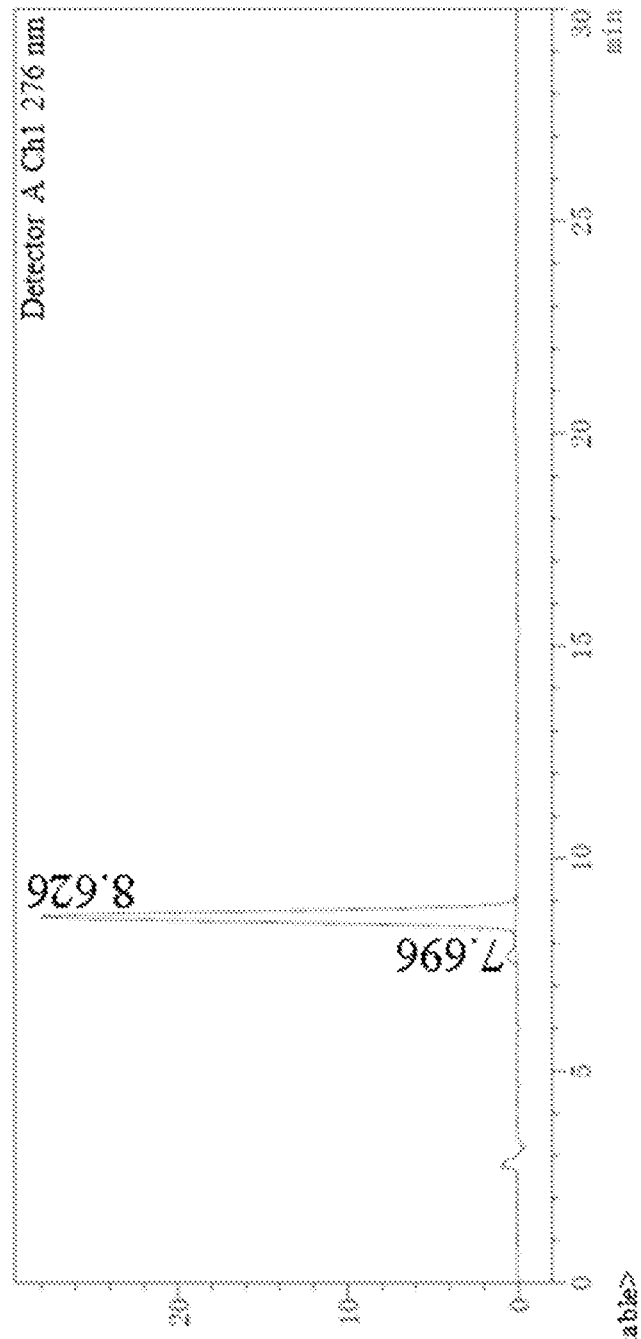
FIG. 4 shows a chromatogram of a reference substance of the compound A.

The chromatographic test results of the test sample solution are shown in FIG. 3, in which the retention time of the compound A is about 8.6 min and the retention time of the compound 1 is about 6.2 min. The chromatographic test results of the reference substance of the compound A are as shown in FIG. 4.

The results are put into Formula I.

In this formula, $A_{sample}$ represents the peak area of the compound A in the test sample solution, with a value of 121719;

$A_{STD}$ represents the peak area of the compound A in the reference substance solution of the compound A, with a value of 483700;

$M_{sample}$ represents the weight (mg) of a test sample, with a value of 100.71 mg;

$M_{STD}$ represents the weight (mg) of the reference substance of the compound A, with a value of 19.89 mg;

$V_{sample}$ represents the volume (mL) of the test sample solution, with a value of 10 mL;

$V_{STD}$ represents the volume (mL) of the reference substance solution of the compound A, with a value of 100 mL; and W represents the content of the reference substance of the compound A, with a value of 98.7%.

After calculation, the content of the compound A in the test sample solution was 0.49%.

3. Sources and detection methods for compounds B and C 3.1 in the first step (an o-acetylsalicycyl chloride production process) of synthesizing the compound 1, the by-product chloroacetylsalicylinyl chloride was produced, which was sourced from the reaction of salicylic acid, produced by the hydrolysis of the raw material aspirin under an acidic condition, with thionyl chloride. The chloroacetylsalicylinyl chloride respectively reacted with diethylaminoethanol in a subsequent reaction step, and continued to form a salt after the subsequent step (injection of hydrogen chloride gas). The presence of this impurity, namely, the compound B, was found both theoretically and in the detection of the finished product.

The product of step 1 in the preparation process of the compound 1 was o-acetylsalicyl chloride, which per se would undergo a cyclization reaction due to the presence of acetyl and acyl chloride groups in the structure of o-acetylsalicyl chloride, resulting in the by-product, 2-chloro-2-methyl-4-hydro-benzo-1,3-dioxin-4-one, which, similarly, due to the presence of chlorine atoms, would react with diethylaminoethanol in a subsequent reaction and continue to form a salt after the subsequent step (injection of hydrogen chloride gas). The presence of this impurity, namely, the compound C, was found both theoretically and in the detection of the finished product.

3.2 Detection method of compounds B and C 3.2.1 Chromatographic conditions: according to high-performance liquid chromatography, octadecylsilane bonded silica gel was used as a filler (250 mm×4.6 mm, 5 μm); the column temperature was 33° C.; the flow rate was 1.0 mL/min; the injection volume was 10 μL; the detection wavelength is 276 nm; and the mobile phase was buffered saline solution-methanol-glacial acetic acid (63:27:10).

3.2.2 Formulation of solutions:

1) Test sample solution: about 100 mg of the crude product of compound 1 was taken as a test sample, weighed accurately, and placed in a 10 mL volumetric flask; methanol was added for dissolution to a constant volume at a given scale; and the mixture was shaken well to be used as a test sample solution, which might be in duplicate upon choice.

2) Reference substance solutions of compounds B and C: about 20 mg of the reference substances of the compounds B and C was taken, weighed accurately, and placed in a 100 mL volumetric flask; methanol was added for dissolution to a constant volume at a given scale; and the mixture was shaken well and used as reference substance solutions of the compounds B and C.

3.2.3 Determination method: the reference substance solutions of the compounds B and C and the test sample solution were accurately weighed out, and respectively injected into a liquid chromatograph; and the chromatograms were recorded, where the chromatograms were recorded till 3 times the retention time of the principal component peak.

3.2.4 Calculation of content $$\text{content of the compound } B, C \text{ (\%)} = \frac{\frac{A_{sample}}{A_{STD}} \times \frac{M_{STD} \times W}{V_{STD}} \times V_{sample}}{M_{sample}} \times 100\% \quad \text{(Formula II)}$$

In the formula;

$A_{sample}$ represents the peak area of the compound B or C in a test sample solution;

$A_{STD}$ represents the peak area of the compound B or C in a reference substance solution of the compound B or C;

$M_{sample}$ represents the weight (mg) of a test sample;

$M_{STD}$ represents the weight (mg) of the reference substance of the compound B or C;

$V_{sample}$ represents the volume (mL) of the test sample solution;

$V_{STD}$ represents the volume (mL) of the reference substance solution of the compound B or C; and W represents the content (calculated as 100.0% in case of above 100%) of the reference substance of the compound B or C.

Figure 5:
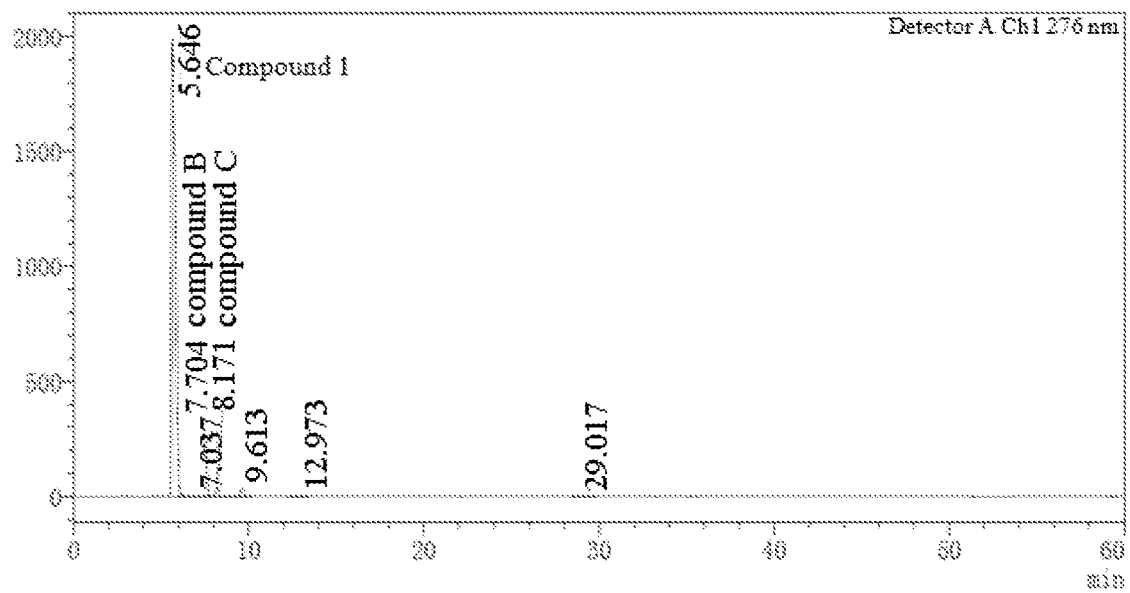
FIG. 5 shows a chromatogram of a crude compound 1.

The peak positions of the compounds B and C under the current chromatographic conditions are shown in FIG. 5, in which the retention time of the compound B is about 7.7 min, the retention time of the compound C is about 8.1 min, and the retention time of the compound 1 is about 5.6 min.

Figure 6:
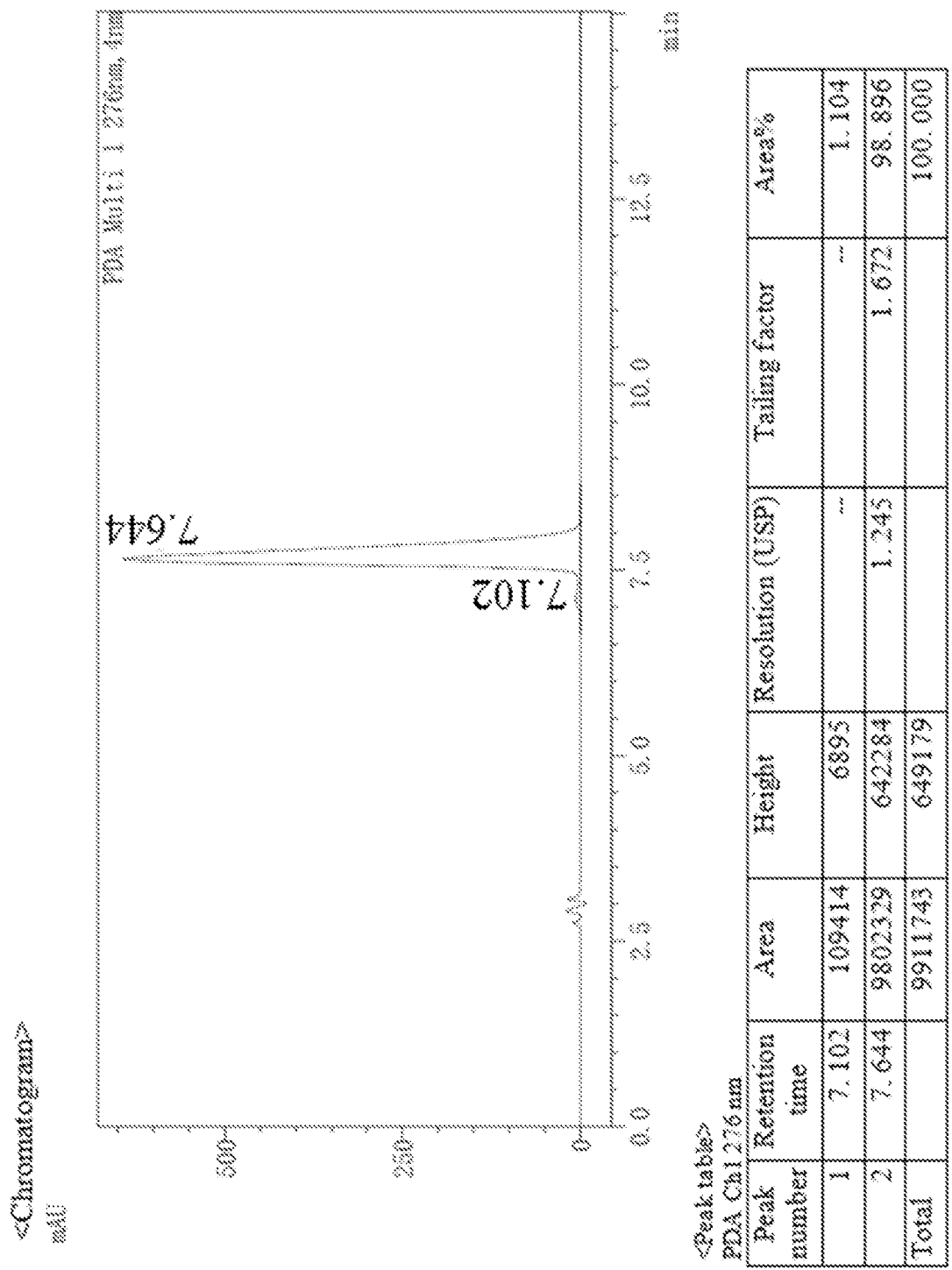
FIG. 6 shows a chromatogram of a reference substance of the compound B.

The results of the reference substance of the compound B are shown in FIG. 6 and put into Formula II. In this formula, $A_{sample}$ represents the peak area of the compound B in the test sample solution of value of 92777;

$A_{STD}$ represents the peak area of the compound B in the reference substance solution of the compound B, with a value of 9802329;

$M_{sample}$ represents the weight (mg) of a test sample, with a value of 99.95 mg;

$M_{STD}$ represents the weight (mg) of the reference substance of the compound B, with a value of 20.21 mg;

$V_{sample}$ represents the volume (mL) of the test sample solution, with a value of 10 mL;

$V_{STD}$ represents the volume (mL) of the reference substance solution of the compound B, with a value of 100 mL; and W represents the content of the reference substance of the compound B, with a value of 99.7%.

After calculation, the content of the compound B in the test sample solution was 0.02%.

Figure 7:
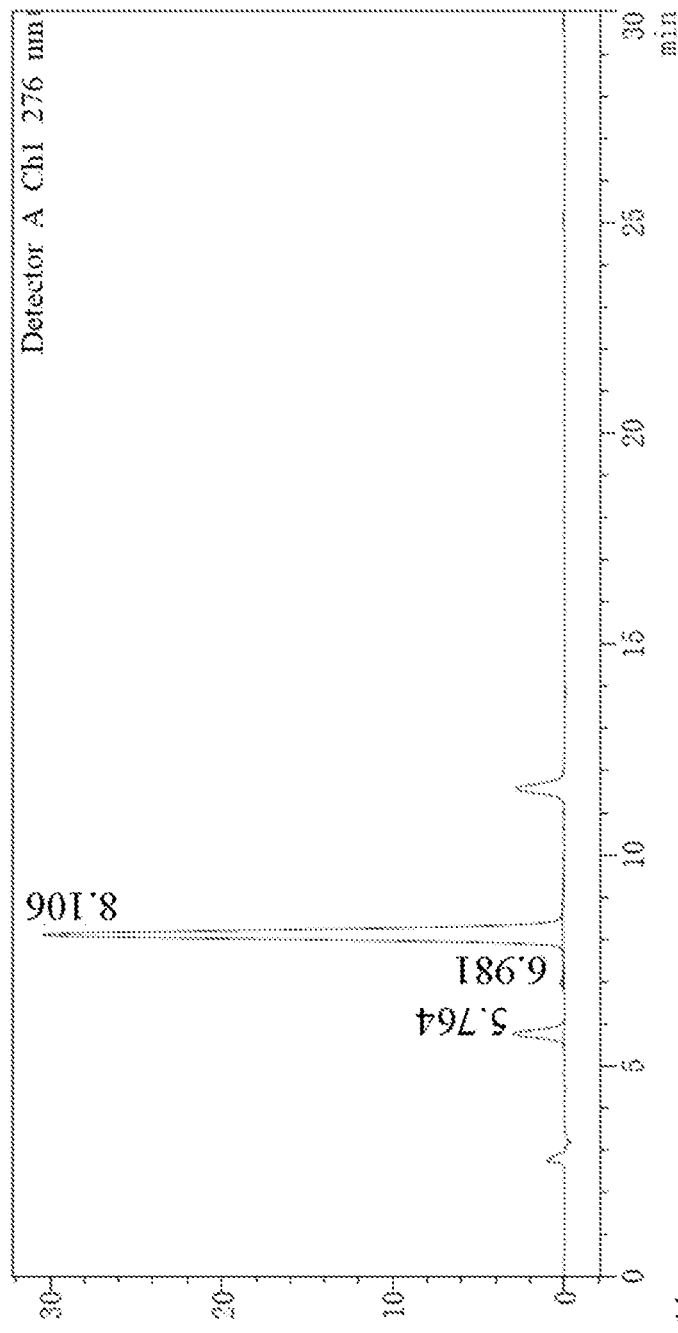
FIG. 7 shows a chromatogram of a reference substance of a compound C.

The results of the reference substance of the compound C are shown in FIG. 7 and put into Formula II. In this formula, $A_{sample}$ represents the peak area of the compound C in the test sample solution, with a value of 68429;

$A_{STD}$ represents the peak area of the compound C in the reference substance solution of the compound C, with a value of 467641;

$M_{sample}$ represents the weight (mg) of a test sample, with a value of 99.95 mg;

$M_{STD}$ represents the weight (mg) of the reference substance of the compound C, with a value of 20.21 mg;

$V_{sample}$ represents the volume (mL) of the test sample solution, with a value of 10 mL;

$V_{STD}$ represents the volume (mL) of the reference substance solution of the compound C, with a value of 100 mL; and W represents the content of the reference substance of the compound C, with a value of 92.5%.

After calculation, the content of the compound C in the test sample solution was 0.27%.

Example 5

This example illustrates, by way of example, that the compounds A, B, C have excellent solubility.

About 0.2 g of the compound (A or B or C) to be tested was weighed and placed into a 10 mL sample tube, 2 mL of purified water was added, and the mixture was mixed well. In case of complete dissolution, about 0.2 g of the compound to be tested was replenished continuously, and the mixture was mixed well until a hypersaturated state was reached or the compound to be tested was added to 2.0 g. If the compound to be tested was added to 2.0 g and is still completely dissolved, the solubility of the compound to be tested in water was recorded as >1.0 g/mL.

Experiments have demonstrated that the solubility of each of the compound A, compound B and compound C is greater than 1.0 g/mL.

Example 6

This example illustrates, by way of example, that the compounds A, B, and C all show dose-dependent inhibition of the level of MCP-1 mRNA, suggesting good anti-inflammatory efficacy.

1. Formulation of Solution:
   1.1 Negative control solution: the negative control was dimethyl sulfoxide (DMSO), which does not need to be formulated and could be used directly.
   1.2 DMEM medium: 1 L of DMEM powder (high sugar, pyruvate) was added to 950 mL of ultrapure water, and 3.7 g anhydrous sodium bicarbonate was added to the medium. The pH value was adjusted to 7.2 with 1 M HCl, and ultrapure water was used to reach the constant volume of 1 L. Finally, the medium was filtered into a sterile container by membrane filtration using a 0.22 μm constant-volume filter. (After filtration, the pH value might rise by 0.1 to 0.3 units)
   1.3 Formulation of positive control drug: a dexamethasone solution: 1.95 mg of dexamethasone was added to 5 mL of DMSO and shaken for dissolution. 1000× solution (10 mM) was obtained. The solution was aliquoted and stored in a refrigerator at −20° C.
   1.4 Formulation of test sample solution:
   Compound A/compound B/compound C: the test sample was weighed at an appropriate mass and dissolved in DMSO to formulate a solution with a final concentration of 1 M, and the solution was aliquoted and then stored at −20° C.
   1.5 Penicillin/streptomycin biantibiotics solution: 8 million units/vial penicillin plus 40 mL of ultrapure water were mixed well, 1 g/vial streptomycin plus 50 mL of ultrapure water were mixed well, the two mixtures were mixed at a volume ratio of 1:1 to obtain 1.00×penicillin-streptomycin biantibiotics solution (containing 100,000 units/mL, penicillin and 10 mg/mL streptomycin). After filtration through a 0.22 μm sterile microfiltration membrane, the solution was aliquoted at 10 mL/tube, and stored in a refrigerator at −20° C.
   1.6 Formulation of buffer solution:
   PBS: 8 g of NaCl, 0.2 g of KCl, 1.44 g of $Na_2HPO_4$ and 0.24 g of $KH_2PO_4$ were respectively weighed and placed in a 1 L volumetric flask; ultrapure water was added to 900 mL; the pH was adjusted to 7.2 with concentrated hydrochloric acid; and the volume was finalized to 1 L. The mixture was stored at room temperature.
2. Cell Culture (Resuscitation, Passaging and Cryopreservation):
   2.1 H9c2 cell resuscitation (source: the Cell Bank of the Chinese Academy of Sciences, stored at 37° C.): the cryovial containing 1 mL of cell suspension was rapidly shaken and thawn in a water bath at 37° C. and mixed well, 4 mL of DMEM complete medium (10% fetal bovine serum (FBS) and 1% penicillin/streptomycin biantibiotics solution) was added, and the mixture was mixed well. The mixture was centrifuged at 1,000 rpm for 4 minutes, the supernatant was discarded, 4 mL of DMEM complete medium was added, and the resultant was homogenized by blowing. All cell suspensions were then added to a T25 cell culture flask and cultured overnight (or the cell suspensions were added to a 10 cm dish, about 6 mL of medium was added, and the mixture was cultured overnight). The cell culture flask was shaken twice horizontally up and down and twice horizontally from side to side, to ensure the even distribution of the cells in the culture flask. The solution was changed the next day, and the cell density was checked.
   2.2 H9C2 cell passaging and plating: If the cell density reached 80%-90%, subculturing could be performed. The culture supernatant was discarded, and the cells were gently shaken from side to side in 500 μL of PBS free of calcium and magnesium ions, for rinsing 1-2 times, and then discarded. 500 μL of trypsin (H9c2 cells used at a concentration of 0.25%) was added to a culture flask, and then placed in an incubator at 37° C. for digestion for 4 min; then, the digestion of the cells was observed under a microscope; after most of the cells became round and fell off, the cells were taken back to the work bench, and 2 mL of DMEM complete medium (the volume ratio of DMEM medium to trypsin=1:4) was added to terminate digestion; and the cells that had not yet fell off were rinsed down with the DMEM complete medium. The DMEM complete medium was replenished based on 6-8 mL/flask, gently beaten well, and sucked; the resultant was centrifuged at 1000 rpm for 6 min, and the supernatant was discarded; and 2 mL of DMEM complete medium was added to resuspend the cells.

If cell passaging was performed, the cell suspension was dispensed, at a ratio of 1:2 to 1:5 ratio, into a new dish containing 8 mL of DMEM complete medium or into a 5 mL T25 cell culture flask.
3. Cell Experiments:
   Screening of anti-inflammatory drugs ley H9c2 cell inflammation model induced by tumor necrosis factor-α (TNF-α)
   H9c2 cells in a 6-well cell culture plate was rinsed twice with PBS after the culture supernatant was discarded, and the cells were incubated with the drug. The experimental wells were set and divided as follows: a blank control group, a model control group, a positive control group and experimental groups. The experimental groups were subdivided into high-dose groups, medium-dose groups, and low-dose groups. After PBS rinsing, 0.98 mL of a DMEM medium (containing 0.5% DMSO) was added to each of the blank group and the model group, and dexamethasone with the final concentration of 10 μM was added to each well in the positive control group. The experimental groups were divided into compound A, compound B and compound C groups with three concentration gradients (i.e., high, medium and low doses) for each drug, and each group was diluted with the DMEM medium. The working concentrations of the compounds A and C were 5 mM, 1 mM, and 0.2 mM, respectively, and the working concentrations of the compound B were 3 mM, 1 mM, and 0.2 mM, respectively. The above solution was added to each well of the 6-well plate and incubated with the cells for 2 h. After 2 h, it was forbidden to discard the DMEM medium, and 20 μL of the DMEM medium containing 500 ng/mL TNF-α was added to each group except for the blank control group, such that the final working concentration of the TNF-α was 10 ng/mL for inducing a cellular inflammatory response. After 1 h, the culture supernatant was discarded, and the cells were rinsed with PBS and then collected for RNA extraction.

4. Processing of Cell Sample:

4.1 Extraction process of total RNA from cells

The total RNA of cells were prepared using a TRizol reagent as follows:

Tissue homogenate: 1 mL of TRizol was added to a 6-well plate containing the cells to scrape the cells off. The cells were pipetted evenly and then transferred into a 1 5 mL EP tube.

Liquid phase separation: 0.2 mL of chloroform was added, and the mixture was shaken vigorously with hands for 15 s, held at room temperature for 2-3 min, and then centrifuged at 4° C. at 12 000 rpm for 15 min. (After centrifugation, the resultant was divided into three layers, with a red lower layer including tissue sediments and a phenol-chloroform phase, a middle layer including proteins and DNA, and an upper layer including a colorless aqueous phase, and RNA existed only in the aqueous phase.)

RNA precipitation and washing: the upper aqueous phase was transferred to another clean EP tube (note that less is better than more, and take care not take the middle layer), 0.5 mL, of isopropanol was added, and the mixture was shaken well with hands, held at room temperature for 10 min, and then centrifuged at 4° C. at 12 000 rpm for 10 min. After centrifugation, white pellets, i.e., RNA pellets, could be seen on the side wall and at the bottom of the tube. The supernatant was removed; 1 mL of 75% ethanol (DEPC water required) was added; the resultant was shaken well upside down, such that the pellets floated at 4° C. and at 7500 rpm for 5 min.

RNA redissolution: the supernatant was gently discarded without losing the pellets; then, the resultant was centrifuged briefly to throw the residual supernatant to the bottom of the tube; and the supernatant was completely sucked with 200 μL and 10 μL pipette guns. The lid was open and the resultant was dried in the air for 5-10 min. The RNA pellets were resuspended with 20-50 μL of DEPC water and repeatedly pipetted with the tip several times.

Concentration measurement: the DEPC water was used as a blank control to measure the OD260/280 value. 1 OD=40 μg RNA. The OD260/280 value in the range of 1.8-2.0 is considered to indicate high purity. Generally, the concentration below 1000 ng/mL is relatively accurate. If the concentration was too high, dilution should be performed before determination. OD260/280 in the range of 1.8-2.0 indicates that the RNA quality is better; OD260/280 greater than 2.2 indicates that RNA has been hydrolyzed to mononucleotides; and OD260/280 less than 1.8 indicates protein contamination. After the RNA extraction was completed, a portion was taken for reverse transcription on the same day; and the remaining was marked well and stored at -80° C.

4.2 Synthesis of first strand of cDNA by reverse transcription of mRNA

The first strand of cDNA was synthesized by reverse transcription of mRNA using a two-step method as follows.

Formulation of reverse transcription reaction system (a 10 μL system): 5×PrimeScript RT Master Mix, total RNA and DEPC water were directly added to the reaction tube, and the mixture was finally gently pipetted for even mixation with a pipette.

TABLE 1

Formulation of reverse transcription reaction system

| Component | Amount |
|---|---|
| 5 × PrimeScript RT Master Mix | 2 μL |
| Total RNA | 500 ng |
| DEPC water | 10 μL |

TABLE 2

Setting of reverse transcription procedures

| Temperature ° C. | Time |
|---|---|
| 37° C. | 15 min |
| 85° C. | 5 sec |
| 4° C. | ∞ |

A reverse transcription product could be used immediately for real-time polymerase chain reaction (qPCR), and could also be stored for a short time at -20° C. In case of long-tem storage, the product is recommended to be stored at -80° C. after aliquoting, in order to avoid repeated freezing and thawing. The cDNA concentration of the reverse transcription product should be measured; DEPC water should be used for the blank zeroing of the instrument; and the measured sample cDNA could be directly used for qPCR detection.

5. Reverse Transcription Polymerase Chain Reaction (RT-PCR) Assay 5.1 Primer design and RT-PCR With the tubulin as an internal reference gene, the primer of the inflammation-related gene MCP-1 of interest was designed and synthesized by Shanghai Personal Biotechnology Co., Ltd. or Sangon Bioengineering (Shanghai) Co., Ltd. Primer information is shown in Table 3 (for H9c2 cells).

TABLE 3

Primer sequences for RT-PCR in rats

| Gene name | Primer name | Sequence (5'-3') |
|---|---|---|
| MCP-1 | Forward | GTCTCAGCCAGATGCAGTTAAT |
|  | Reverse | AGTTCTCCAGCCGACTCATTG |
| Tubulin | Forward | TAGCAGAGATCACCAATGCC |
|  | Reverse | GGCAGCAAGCCATGTATTTA |

5.2 RT-PCR

With cDNA, as a template, the RT-PCR system was formulated using SYBR Premix Ex TaqTMII (Tli RNaseH Plus) (Table 4). The reaction was performed using the Roche Light Cycle 480II 96 Real-Time PCR System, with the amplification procedures as follows: predenaturation at 95° C. for 30 s, denaturation at 95° C. for 5 s, annealing at 55° C. for 30 s, and extension at 72° C. for 30 s, for 40 cycles; addition of melting curves; and detection of fluorescence signals at the end of each cycle.

TABLE 4

RT-PCR system

| Reagent | Amount | Final concentration |
|---|---|---|
| SYBR Premix Ex TaqTM | 10 μL | 1× |
| PCR forward primer (10 μM) | 0.8 μL | 0.4 μM*1 |

TABLE 4-continued

| RT-PCR system | | |
|---|---|---|
| Reagent | Amount | Final concentration |
| PCR reverse primer (10 μM) | 0.8 μL | 0.4 μM*1 |
| cDNA template | 2.0 μL | |
| dH$_2$O | 6.4 μL | |
| Total | 20.0 μL | |

6. Test Groups and Methods 6.1 Grouping and dosage information

TABLE 5

| Grouping and dosage information | | |
|---|---|---|
| Group | Drug | Concentration |
| Positive control | Dexamethasone | 10 μM |
| Test sample 1 | Compound C | 5/1/0.20 mM |
| Test sample 2 | Compound B | 3/1/0.20 mM |
| Test sample 3 | Compound A | 5/1/0.20 mM |

6.2 Test Method 6.2.1 Modeling method

The H9c2 cell inflammation induction model was modeled under the following conditions: induced by 10 ng/mL TNF for 1 h.

6.2.2 Determination of efficacy index

Figure 8:
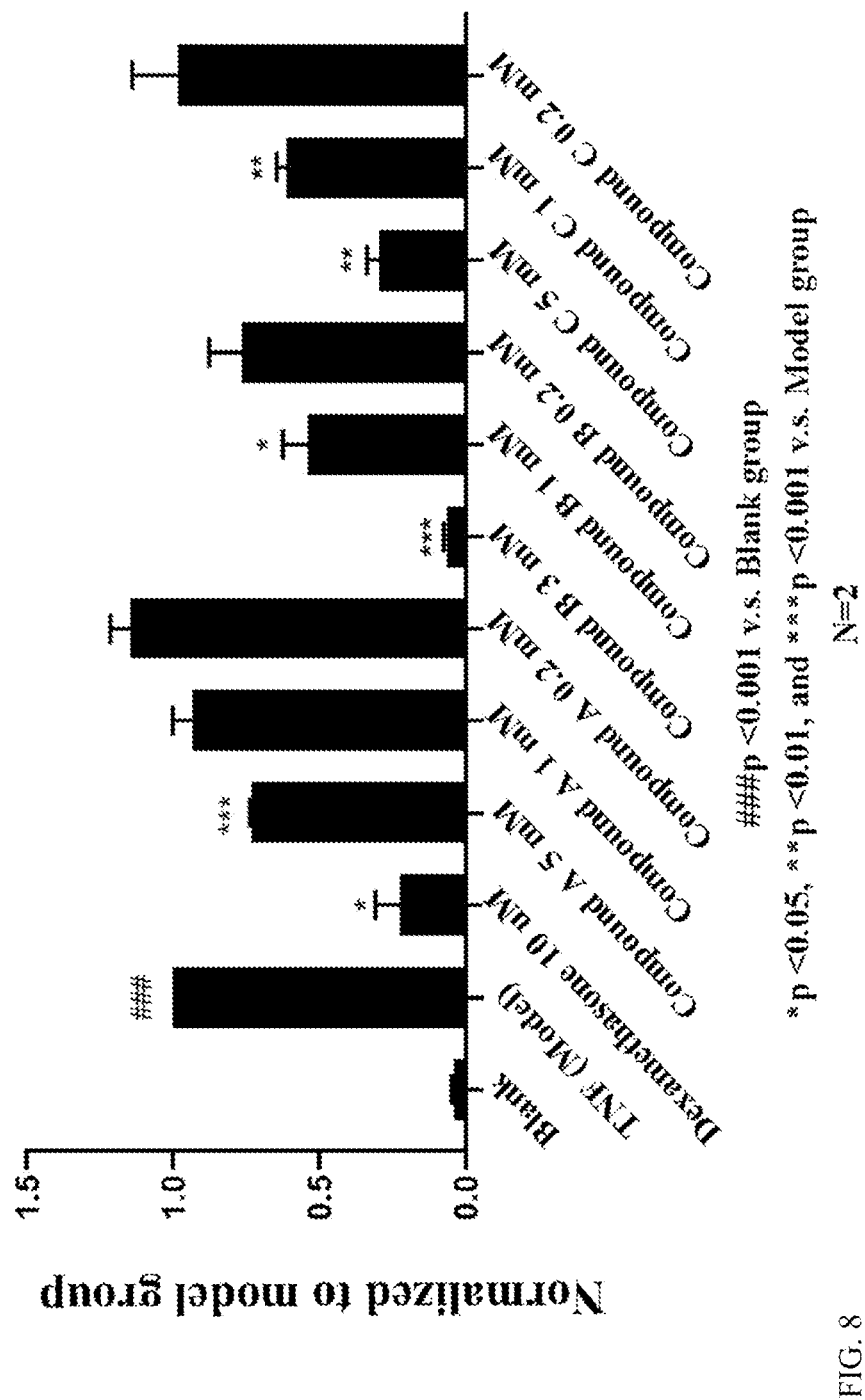
FIG. 8 shows the expression of inflammatory factor monocyte chemoattractant protein 1 (MCP-1) mRNA in a reverse transcription-polymerase chain reaction (RT-PCR) assay.

The inflammatory factor MCP-1 was selected as an anti-inflammatory efficacy index for the H9c2 cell model. The expression of the mRNA of the inflammatory factor MCP-I was detected by RT-PCR. See FIG. 8.

7. Conclusion

In the TNF induced H9c2 cell model, the compounds A, B and C show the dose-dependent inhibition of the elevation of the mRNA, level of the inflammatory factor MCP-1 in certain dose range. It indicates that the compounds A, B and C have an anti-inflammatory activity.

The invention claimed is:

1. A compound having a formula selected from the group consisting of:

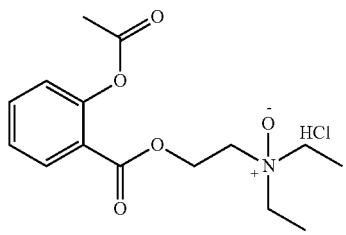

Compound A

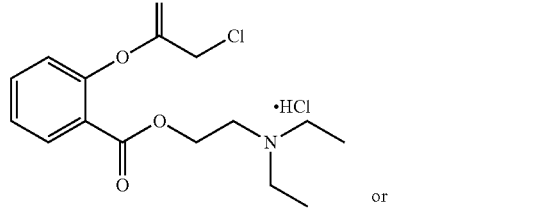

Compound B or

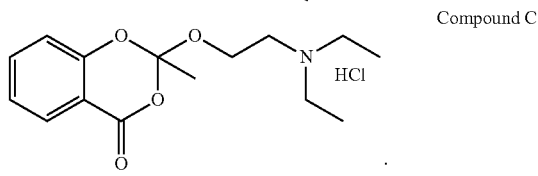

Compound C

2. A product containing 2-(diethylamino)ethyl 2-acetoxybenzoate hydrochloride, wherein, said product comprises said 2-(diethylamino)ethyl 2-acetoxybenzoate hydrochloride having a content of not less than 98.00% by weight, and impurity compounds; said impurity compounds are selected from the group consisting of said compound A, compound B or compound C according to claim 1, or a combination thereof; and any one of said impurity compounds has a content of less than or equal to 0.50% by weight.

3. The product according to claim 2, wherein, said product comprises said 2-(diethylamino)ethyl 2-acetoxybenzoate hydrochloride having a content of not less than 99.00% by weight.

4. The product according to claim 2, wherein, said impurity compounds have a content of less than or equal to 0.30% by weight.

5. The product according to claim 4, wherein said impurity compounds have a content of less than or equal to 0.20% by weight.

6. The product according to claim 4, wherein said impurity compounds have a content of less than or equal to 0.10% by weight.

* * * * *